United States Patent
Breuer et al.

(10) Patent No.: US 7,101,864 B1
(45) Date of Patent: Sep. 5, 2006

(54) COMPOSITIONS COMPRISING OXOPHOSPHONATE-BASED METALLOPROTEINASE INHIBITORS

(75) Inventors: Eli Breuer, Jerusalem (IL); Reuven Reich, Rehovot (IL); Claudio Salomon, Rosario (AR)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 99 days.

(21) Appl. No.: 10/110,317

(22) PCT Filed: Sep. 19, 2000

(86) PCT No.: PCT/IL00/00579

§ 371 (c)(1),
(2), (4) Date: Sep. 13, 2002

(87) PCT Pub. No.: WO01/26661

PCT Pub. Date: Apr. 19, 2001

(30) Foreign Application Priority Data

Oct. 11, 1999 (IL) .................... 132315

(51) Int. Cl.
*A61K 31/662* (2006.01)
*C07F 9/38* (2006.01)

(52) U.S. Cl. .................. 514/114; 558/170; 558/178

(58) Field of Classification Search .................. None
See application file for complete search history.

(56) References Cited

FOREIGN PATENT DOCUMENTS

EP    107456    5/1984

*Primary Examiner*—Kamal A. Saeed
(74) *Attorney, Agent, or Firm*—Browdy and Neimark, PLLC

(57) ABSTRACT

The present invention relates to compositions useful for treating or controlling disease states or conditions associated with zinc containing proteinases, especially metalloproteinases. The active ingredient in these compositions is an alpha-oxo- or alpha-thixophosphpnate of formula (I). Out of the phosphonates of formula (I), some are known and others are new. The novel compounds constitute another aspect of the invention.

13 Claims, No Drawings

COMPOSITIONS COMPRISING OXOPHOSPHONATE-BASED METALLOPROTEINASE INHIBITORS

FIELD OF THE INVENTION

This invention relates to compositions useful for treating or controlling disease states or conditions associated with zinc containing proteinases, especially matrix metalloproteinases.

BACKGROUND OF THE INVENTION

Inhibition of matrix metalloproteinases (MMPs) as an approach to treat diseases such as cancer, arthritis or multiple sclerosis is now an area of intense interest within the pharmaceutical industry (see P. R. Beckett & M. Whittaker in Exp. Opin. Ther. Patents (1998) 8,259–282).

MMPs are a family of zinc-containing calcium dependent enzymes, including stromelysins, collagenases and gelatinases. Approximately nineteen MMPs have been identified. MMPs are capable of degrading and remodeling many proteinaceous components of the extracellular matrix in both physiological and pathological conditions. Misregulation and overexpression of MMPs is believed to be a major factor in a number of disease states, most of them characterized by unwanted degradation of connective tissue. These include rheumatoid arthritis, tumor invasion, metastasis, angiogenesis, multiple sclerosis, periodontal disease, coronary artery disease, restenosis, congestive heart failure, wound healing, bone matrix degradation, osteoporosis, liver cirrhosis, cerebral ischemia, meningitis and others.

Other zinc-containing proteinases include Angiotensin Converting Enzyme (ACE), Endothelin Converting Enzyme (ECE) and Adamalysins, the inhibition of which may be of considerable clinical importance.

Compounds which contain a zinc binding function may prevent the catalytic activity of zinc-containing proteinases, for example of MMPs, since they block the zinc atom from fulfilling its catalytic role at the enzyme's active site. MMP (and other zinc-containing proteinases) inhibiting activity has been found in certain hydroxamates, sulfonamide hydroxamates, phosphonates, phosphinates, phosphonamidates, thiols, carboxylates or peptides (P. R. Beckett & M. Whittaker in Exp. Opin. Ther. Patents (1998) 8, 259–282).

Alpha-oxophosphonates, also known such as acylphosphonates have been shown to be capable to chelate various metal ions, such as calcium (M. Mathew et al., Inorg. Chem. (1998) 37, 6485–6494). However, there is no existing record showing that alpha-oxophosphonates inhibit MMPs or other zinc-containing proteinases.

Phosphonoformyl amine derivatives were described in P. Wieczorek et al., Pestic. Sci. (1994), 40 57–62 as having herbicidal activity. In addition, N-phosphonoformyl amino acid derivatives were described in DD 242811 as having antiviral activity.

SUMMARY OF THE INVENTION

In accordance with the present invention, it has been surprisingly found that alpha-oxo- or alpha-thioxophosphonates have a remarkable inhibiting effect on zinc-containing proteinases, especially on MMPs and thus inhibit the invasiveness of cancer cells.

Preferred phosphonates which may be used in accordance with the invention are those of the following formula I

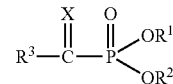

wherein $R^1$ and $R^1$ may be the same or different and are each selected from hydrogen, alkyl, haloalkyl, acyloxyalkyl, aryl, an alkali metal cation or an optionally substituted ammonium cation or $R^1$ and $R^1$ may form together with the oxygen and phosphorus atoms a dioxaphosphacycloalkane ring;

$R^3$ is selected from the group consisting of alkyl, aryl, aralkyl, cycloalkyl, heteroaryl, heteroaralkyl, heterocyclyl, heterocyclyl-substituted lower alkyl, optionally substituted $C_1$–$C_{10}$ aminoalkyl or $C_3$–$C_{10}$ aminocycloalkyl, —OZ or —SZ where Z is selected from optionally substituted alkyl, cycloalkyl, aralkyl, aryl, or $R^3$ is —$NR^4R^5$ where $R^4$ and $R^5$ may be the same or different and are each selected from hydrogen, hydroxy, alkyl, cycloalkyl, alkoxy, aryl, heteroaryl, aralkyl, heteroaralkyl, alkoxyalkyl, carboxyalkyl, alkoxycarbonylalkyl, aryloxycarbonylalkyl, acyloxyalkoxycarbonylalkyl, heterocyclyl, heterocyclyl-substituted lower alkyl, $C_1$–$C_{10}$ aminoalkyl or aminocycloalkyl, guanidinoalkyl, guanidinocycloalkyl, amidinoalcyl, amidinocycloalkyl or $R^3$ is an amino acid or an oligopeptide, said aminoacid or oligopeptide optionally being substituted at its N-terminus and/or at its C-terminus; X is O or S; or a pharmaceutically acceptable salt thereof.

The present invention thus provides the use of a compound of the general formula I above or a pharmaceutically acceptable salt thereof, for the preparation of a medicament for treating or controlling disease states or conditions associated with zinc containing proteinases, especially matrix metalloproteinases.

The present invention also provides a method of treating mammals having disease states alleviated by the inhibition of zinc containing proteinases, comprising administering to an individual in need an effective amount of a compound of the general formula I or a pharmaceutically acceptable salt thereof.

The present invention still further provides a pharmaceutical composition for treating or controlling disease states or conditions associated with zinc containing proteinases, especially matrix metalloproteinases, comprising as an active ingredient a compound of the general formula I or a pharmaceutically acceptable salt thereof together with a pharmaceutically acceptable carrier.

Out of the phosphonates of formula I, some are known and others are new. The novel compounds constitute another aspect of the invention. Further aspects of the present invention are the use of these new compounds in the preparation of medicaments and pharmaceutical compositions comprising them as active ingredients.

Definitions

The term "effective amount" is meant to denote an amount of the active ingredient (the phosphonate of formula I above, or a pharmaceutically acceptable salt thereof) which is effective in achieving the desired therapeutic result, namely inhibition of zinc containing proteinases, especially matrix metalloproteinases. The effective amount may depend on a number of factors including: the dosage form, the age group of the treated individual and his weight, the mode of administration of the active ingredient, the type of carrier being used (e.g. whether it is a carrier that rapidly releases the active ingredient or a carrier that releases it over a period of time), as well as on various other factors as known per se. The artisan, by routine type experimentation should have no substantial difficulties in determining the effective amount in each case.

"Alkyl" means a linear or branched saturated hydrocarbon radical of up to ten carbon atoms, e.g. methyl, ethyl, propyl, 2-propyl, pentyl and the like, optionally substituted, for example by a cycloalkyl thus forming substituents such as cyclohexylmethyl, cycloheptylethyl and the like, optionally substituted by a mercapto function or optionally containing sulfide function in the hydrocarbon chain.

"Halo" means fluoro, chloro, bromo or iodo, preferably fluoro and chloro.

"Haloalkyl" means alkyl substituted with one or more same or different halogen atoms, e.g. —$CH_2Cl$, —$CF_3$, —$CH_2CF_3$, $CH_2CCl_3$ and the like.

"Cycloalkyl" means a saturated cyclic or bicyclic hydrocarbon radical of three to twelve carbons, e.g. cyclopropyl, cyclopentyl, cyclohexyl, bicycloheptyl and the like, optionally substituted with one or more substituents independently selected from alkyl, cycloalkyl, haloalkyl, halo, acyloxy, acyloxyalkyl, amino, hydroxy, alkoxy, carboxyalkyl, —COOH, alkylamino and aminocycloalkyl.

"Aryl" means a monocyclic or bicyclic aromatic hydrocarbon radical of 6 to 10 ring atoms and optionally substituted with one or more substituents, independently selected from alkyl, cycloalkyl, haloalkyl, halo, acyloxy, acyloxyalkyl, cycloalkyl, amino, alkylamino, cycloalkylamino, —OR, —C(O)R or COOH, or optionally substituted aryl, optionally substituted aralkyl, heteroaryl, heteroaralkyl.

"Heteroaryl" means a monocyclic or bicyclic aromatic radical of 5 to 10 ring atoms containing one, two or three heteroatoms selected from N, O or S, preferably N, the remaining atoms being C. The heteroaryl ring is optionally substituted with one or more substituents, independently selected from alkyl, cycloalkyl, haloalkyl, halo, acyloxy, acyloxyalkyl, cycloalkyl, amino, alkylamino, cycloalkylamino, —OR, —C(O)R or COOH, or optionally substituted aryl, optionally substituted aralkyl, heteroaryl, heteroaralkyl.

"Heterocyclyl" means a saturated cyclic radical of 3 to 8 ring atoms in which one or two ring atoms are heteroatoms selected from N, O, S or $S(O)_n$ (where n is an integer from 0 to 2), the remaining atoms being C, where one or two C atoms may optionally be replaced by a carbonyl group. The heterocyclyl may be optionally substituted with one or more substituents, independently selected from alkyl, cycloalkyl, haloalkyl, halo, acyloxy, acyloxyalkyl, cycloalkyl, amino, alkylamino, cycloalkylamino, —OR, —C(O)R or COOH, or optionally substituted aryl, optionally substituted aralkyl, heteroaryl, heteroaralkyl.

"Aralkyl" means a radical which consists of an aryl and an alkylene group, e.g. benzyl, phenylethyl and the like. The aryl moiety in aralkyl may optionally be substituted with one or more substituents, independently selected from alkyl, cycloalkyl, haloalkyl, halo, acyloxy, acyloxyalkyl, cycloalkyl, amino, alkylamino, cycloalkylamino, —OR, —C(O)R or COOH, or optionally substituted aryl, optionally substituted aralkyl, heteroaryl, heteroaralkyl.

DETAILED DESCRIPTION OF THE INVENTION

As stated above, preferred phosphonates of formula I for use in accordance with the invention are those of the following formula I

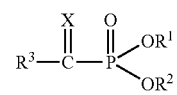

I wherein $R^1$ and $R^2$ may be the same or different and are each selected from hydrogen, alkyl, haloalkyl, acyloxyalkyl, aryl, an alkali metal cation or an optionally substituted ammonium cation or $R^1$ and $R^2$ may form together with the oxygen and phosphorus atoms a dioxaphosphacycloalkane ring;

$R^1$ is selected from the group consisting of alkyl, aryl, aralkyl, cycloalkyl, heteroaryl, heteroaralkyl, heterocyclyl, heterocyclyl-substituted lower alkyl optionally substituted $C_1$–$C_{10}$ aminoalkyl or $C_3$–$C_{10}$ aminocycloalkyl, —OZ or —SZ where Z is selected from optionally substituted alkyl, cycloalkyl, aralkyl, aryl, or $R^3$ is —$NR^4R^5$ where $R^4$ and $R^5$ may be the same or different and are each selected from hydrogen, hydroxy, alkyl, cycloalkyl, alkoxy, aryl heteroaryl, aralkyl, heteroaralkyl, alkoxyalkyl, carboxyalkyl, alkoxycarbonylalkyl, aryloxycarbonylalkyl, acyloxyalkoxycarbonylalkyl heterocyclyl, heterocyclyl-substituted lower alkyl $C_1$–$C_{10}$ aminoalkyl or aminocycloalkyl, guanidinoalkyl, guanidinocycloalkyl, amidinoalkyl, amidinocycloalkyl or $R^3$ is an aminoacid or an oligopeptide, said aminoacid or oligopeptide optionally being substituted at its N-terminus and/or at its C-terminus; X is O or S; or pharmaceutically acceptable salt thereof.

Examples of phosphonates of formula I above are shown in Table 1. These compounds may generally be synthesized using methods known in the art for the synthesis of alpha-oxo- or alpha-thioxophosphonates. Specific methods that may typically be used are described below in the Examples.

Table 1 further shows the inhibitory effect of these compounds on MMPs. As a consequence of this effect the invasiveness of cancer cells is inhibited. The compounds examined have been added to the invasion or chemotaxis chambers respectively, at various concentrations. The resulted invasion and migrations were compared to untreated preparations and initially grouped according to their activity; '++++' denotes compounds that were active at submicromolar concentration, '+++'-compounds were active at 1–10 μM, '++' were active at 50–100 μM, '+' were active at 100 μM, '–' compounds were not active at 100 μM.

TABLE 1

| # | Compound | Solvent | Activity |
|---|---|---|---|
| 1 | HO-N(Me)-C(=O)-P(=O)(OEt)(ONa) | $H_2O$ | ++ |
| 2 | Et-S-C(=O)-P(=O)(OH)(ONa) | $H_2O$ | +++ |
| 3 | nPr-S-C(=O)-P(=O)(OH)(ONa) | $H_2O$ | +++ |
| 4 | $Cl_3CCH_2$-O-C(=O)-P(=O)(OH)(ONa) | $H_2O$ | ++ |
| 5 | $PhCH_2$-O-C(=O)-P(=O)(OH)(ONa) | $H_2O$ | ++ |
| 6 | $pClC_6H_4$-O-C(=O)-P(=O)(OH)(ONa) | $H_2O$ | +++ |
| 7 | PhC(=O)-P(=O)(OH)(ONa) | $H_2O$ | ++ |
| 8 | $pClC_6H_4$C(=O)-P(=O)(OH)(ONa) | $H_2O$ | +++ |
| 9 | $pClC_6H_4$C(=O)-P(=O)(OMe)(ONa) | $H_2O$ | − |
| 10 | $C_2H_5$C(=O)-P(=O)(OH)(ONa) | $H_2O$ | + |
| 11 | $C_2H_5$C(=O)-P(=O)(OMe)(ONa) | $H_2O$ | + |
| 12 | $PhCH_2$C(=O)-P(=O)(OH)(ONa) | $H_2O$ | + |
| 13 | $PhCH_2$C(=O)-P(=O)(OMe)(ONa) | $H_2O$ | ++ |
| 14 | $CH_3CH_2$C(=NOH)-P(=O)(OMe)(OLi) | $H_2O$ | + |
| 15 | $pClC_6H_4$-NHC(=O)-P(=O)(OEt)(ONa) | $H_2O$ | + |

TABLE 1-continued
| # | Compound | Solvent | Activity |
|---|---|---|---|
| 16 | 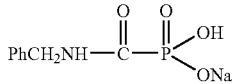 | H₂O | ++ |
| 17 | 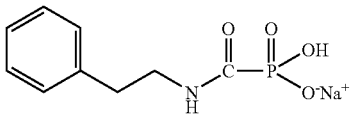 | H₂O | + |
| 18 | 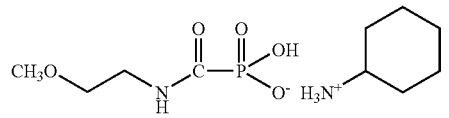 | H₂O | ++ |
| 19 | 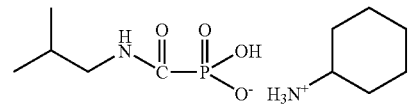 | H₂O | + |
| 20 | 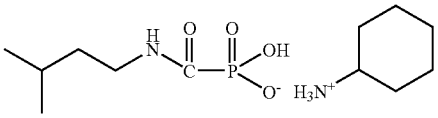 | H₂O | + |
| 21 | 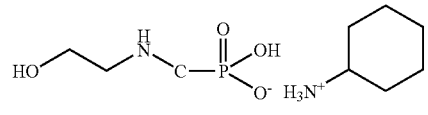 | H₂O | + |
| 22 | 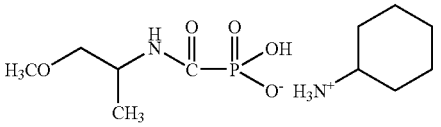 | H₂O | + |
| 23 | 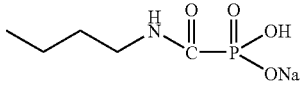 | H₂O | + |
| 24 | 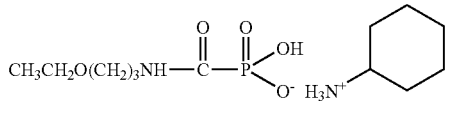 | H₂O | + |
| 25 | 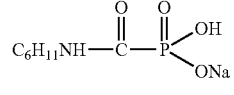 | H₂O | ++++ |
| 26 | 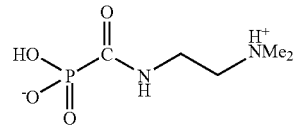 | H₂O | ++++ |
| 27 | 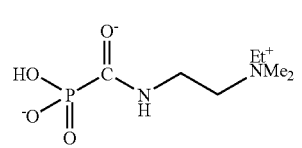 | H₂O | ++++ |

TABLE 1-continued

| # | Compound | Solvent | Activity |
|---|----------|---------|----------|
| 28 | Phosphono-carbamoyl lysine derivative with CONHMe and $^+NH_3$ groups | $H_2O$ | ++++ |
| 29 | Phosphono-carbamoyl ethyl-$^+NMe_3$ | $H_2O$ | ++++ |
| 30 | Phosphono-carbamoyl propyl-$H^+NMe_2$ | $H_2O$ | ++++ |
| 31 | Phosphono-carbamoyl butyl-guanidinium | $H_2O$ | ++++ |
| 32 | Phosphono-carbamoyl propyl-$^+NMe_3$ | $H_2O$ | ++++ |
| 33 | Phosphono-thiocarbamoyl cyclohexyl | Ethanol | ++++ |
| 34 | Phosphono-thiocarbamoyl ethyl-$^+NMe_2H$ | $H_2O$ | ++++ |
| 35 | Phosphono-carbamoyl derivative with CONHMe, $C_6H_5$, NaO | $H_2O$ | +++ |
| 36 | $CH_3O$-glycine-carbamoyl-phosphonate, $H_3N^+$-cyclohexyl | $H_2O$ | +++ |
| 37 | Phosphono-carbamoyl arginine with CONHMe | $H_2O$ | ++++ |
| 38 | $ClC_6H_4CH_2PO_3HNa$ | $H_2O$ | − |

Preferred compounds of formula I for use in the compositions of the present invention are phosphonoformamides (also known as carbamoylphosphonates). Particularly preferred compounds in accordance with the invention are the novel compounds 25–37 shown in Table 1 above.

The active ingredients, i.e. alpha-oxo- or alpha-thioxo-phosphonates used in accordance with the invention may be formulated into pharmaceutical compositions by any of the conventional techniques known in the art. The pharmaceutical carrier may be solid or liquid.

The compositions may be prepared in various forms such as capsules, tablets, suspensions, suppositories or injectable formulations for parenteral, e.g. intramuscular or intravenous injection. In tablets for example, the active ingredient is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, methyl cellulose, sodium carboxymethyl cellulose and polyvinylpyrrolidine. Liquid carriers may be used in preparing solutions, suspensions, emulsions or syrups. The active ingredient can be dissolved or suspended in a pharmaceutically acceptable liquid carrier such as water, an organic solvent, a mixture of pharmaceutically acceptable oils or fat. Suitable examples of liquid carriers for oral and parenteral administration include water, alcohols, and oils.

The preferred administration form in each case will depend on the desired delivery mode (which is usually that which is the most physiologically compatible in accordance with the patient's condition), other therapeutic treatments which the patient receives, etc.

Without wishing to be bound by theory, it is believed that the alpha-oxo or alpha-thioxo function in the phosphonates of the present invention is necessary for the inhibitory effect on zinc containing proteinases, especially MMPs. This is apparent from comparing the effect of p-chlorobenzylphosphonic acid sodium salt ($ClC_6H_4CH_2PO_3HNa$, compound 38 in Table 1) to that of p-chlorobenzoylphosphonic acid sodium salt ($ClC_6H_4C(O)PO_3HNa$, compound 8 in Table 1). While the latter shows considerable MMP inhibiting activity at a concentration of 10 micromolar the former, having the same structure except for the lack of the oxygen at the alpha position, is completely devoid of inhibitory activity.

Out of the phosphonates of formula I, some are known, albeit for uses other than those of the compositions of the invention, and others are novel. The novel compounds of formula I which constitute another aspect of the invention are carbamoylphosphonates shown below:

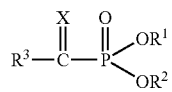

I wherein $R^1$ and $R^2$ may be the same or different and are selected from hydrogen, an alkali metal cation or an optionally substituted ammonium cation;

$R^3$ is selected from the group consisting of —$NR^4R^5$ where $R^4$ and $R^5$ may be the same or different and are each selected from hydrogen, alkyl, cycloalkyl, alkoxy, aryl, heteroaryl, aralkyl, heteroaralkyl, alkoxyalkyl, carboxyalkyl, alkoxycarbonylalkyl, aryloxycarbonylalkyl, acyloxyalkoxycarbonylalkyl heterocyclyl, heterocyclyl-substituted lower alkyl, $C_1$–$C_{10}$ aminoalkyl or $C_3$–$C_{10}$ aminocycloalkyl, morpholino, guanidinoalkyl, guanidinocycloalkyl, amidinoalkyl, amidinocycloalkyl or $R^3$ is an amino acid or an oligopeptide, said amino acid or oligopeptide optionally being substituted at its N-terminus and/or at its C-terminus; X is O or S, or a pharmaceutically acceptable salt thereof.

Particularly preferred new compounds in accordance with the invention are those having formula I, wherein $R^3$ is 2-dimethylaminoethylamino (compound #26 in Table 1), cyclopentylamino, 2-(4-imidazolylethl)amino, or an oligopeptide, said oligopeptide optionally being substituted at its C-terminus, for example phosphonoformyl-Leu-Val-NHMe, phosphonoformyl-Phe-Val-NHMe, phosphonoformyl-Leu-Phe-phenethylamide, phosphonoformyl-Leu-Tyr(Me)-N-methylamide and phosphonoformyl-Leu-Phe-N-methylamide. These compounds were found active in the Boyden chamber chemoinvassion assay at 1 µM concentrations or less and the structures of some of them are shown below:

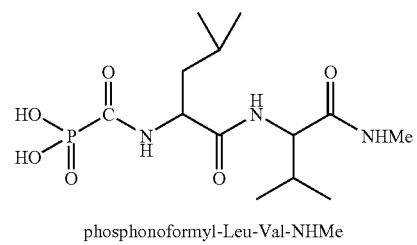

phosphonoformyl-Leu-Val-NHMe

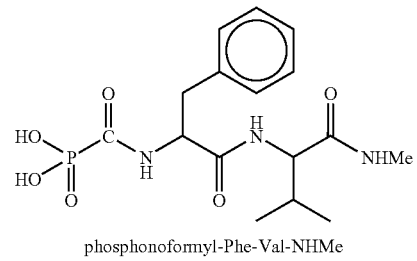

phosphonoformyl-Phe-Val-NHMe

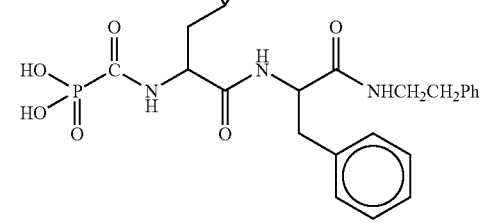

phosphonoformyl-Leu-Phe-phenethylamide

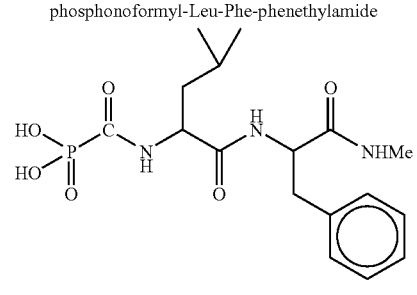

phosphonoformyl-Leu-Phe-methylamide

The invention will now be illustrated by the following non-limiting examples.

EXAMPLES

Synthetic Examples

Example 1 p-Chlorobenzoylphosphonic acid

To a solution of dimethyl p-chlorobenzoylphosphonate (1 mmol) in dry dioxane (5 ml), BrMe$_3$Si (3 mmol) was added dropwise under magnetic stirring, in nitrogen atmosphere at room temperature. After 5 h the solvent was removed under vacuum and the brown residue was dissolved in MeOH at 0° C. The solvent was evaporated and a solution of NaOH (1 mmol) in MeOH (5 ml) was added in portions. The white solid was filtered and dried under vacuum. Yield: 76%. NMR, $^1$H: 7.54 (d, 2H), 8.11 (d, 2H); $^{31}$P, −1.48 ppm.

Example 2

Sodium phosphonyl ethylthiolformate a) Triethyl phosphite (1 mmol) was added to ethyl chlorothiolformate (1 mmol) at 0° C. under N$_2$ atmosphere and the resulting mixture was magnetically stirred at room temp. Monitoring the reaction by $^{31}$P NMR showed that after 3 h the reaction was completed. The clear yellow solution was purified by distillation (b.p. 110–114° C. at 1 mm). Yield of the product triethyl phosphonothiolformate: 81%, NMR, $^1$H, 1.27 (t, 3H); 1.36 (t, 6H); 2.99 (c, 2H), 4.23 (m, 4H). $^{31}$P −4.22 ppm.

b) To a solution of triethyl phosphonothiolformate (1 mmol), prepared in step a), in dry dioxane (5 ml), BrMe$_3$Si (3 mmol) was added dropwise under magnetic stirring and N$_2$ atmosphere, at 60° C. After 10 h the solvent was removed under vacuum and the brown residue dissolved in MeOH at 0° C. The solvent was evaporated and a solution of NaOH (1 mmol) in MeOH (5 ml) was added in portions. The white solid was filtered and dried under vacuum. Yield: 76%. $^1$H NMR: 1.20 (t, 3H); 2.90 (c, 2H). $^{31}$P NMR: −1.37 ppm.

Example 3

N-Cyclohexyl(diisopropylphosphonylformamide)

To a solution of cyclohexylamine (1 mmol) in acetonitrile (5 mL) diisopropyl ethyl phosphonothiolformate (1 mmol) was added dropwise under magnetic stirring, in N$_2$ atmosphere at 0° C. The reaction was monitored by $^{31}$P NMR. It was complete after 8 h. The solvent was evaporated under vacuum and the crude product was dissolved in AcOEt, and purified by chromatography. Yield: 62%, NMR, $^1$H, 1.10–1.30 (m, 5H); 1.35 (t, 12H); 1.60–1.95 (m, 5H); 3.82 (m, 1H); 4.75 (m, 2H); 6.82 (m, 1H). $^{31}$P NMR: −2.48 ppm.

Example 4

N-Cyclohexyl(diethylphosphonylformamide)

To a solution of cyclohexylamine (1 mmol) in acetonitrile (5 mL) triethyl phosphonoformate (1 mmol) was added dropwise under magnetic stirring, in N$_2$ atmosphere at ambient temperature. The reaction was monitored by $^{31}$P NMR. It was complete after 20 h. The solvent was evaporated under vacuum and the crude product was dissolved in AcOEt, and purified by chromatography. Yield: 80%.

Example 5

Hydrogen sodium N-cyclohexylcarbamoylphosphonate

To a solution of N-cyclohexyl(diisopropylphosphonylformamide) (1 mmol) prepared in Example 3, in dry dioxane (5 ml), bromotrimethylsilane (5 mmol) was added dropwise under magnetic stirring, in a N$_2$ atmosphere at 60° C. After 10 h the solvent was removed under vacuum and the brown residue was dissolved in MeOH at 0° C. The solvent was evaporated and a solution of NaOH (1 mmol) in MeOH (5 ml) was added in portions. The white solid was filtered and dried under vacuum. Yield: 76%, NMR, $^1$H, 1–1.20 (m, 5H); 1.40–1.69 (m, 5H); 3.58 (m, 1H). $^{31}$P, −2.56 ppm. The same compound was prepared also by dealkylation of N-cyclohexyl(diethylphosphonylformamide) prepared in Example 4 above, by bromotrimethylsilane in dry acetonitrile at room temperature. The product was isolated in the same manner.

Examination of the activity of the product on pure MMP2 enzyme gave an IC$_{50}$ value of 80 nM. In the Boyden chamber chemoinvasion assay the compound was active at 1 µM.

Example 6

N-(2-dimethylaminoethyl)phosphonoformamide betaine a) To a solution of N,N-dimethylethylenediamine (1 mmol) in acetonitrile (5 mL), triethyl phosphonothiolformate (1 mmol), prepared in Example 2, was added dropwise under magnetic stirring, in N$_2$ atmosphere at 0° C. After 2 h the solvent was evaporated under vacuum. The residue, consisting of diethyl N-(2-dimethylaminoethyl)phosphonoformamide betaine was practically pure. $^1$H nmr (CDCl$_3$): 7.45 ppm (1H, broad), 4.19 (4H, m), 3.35 (2H, m), 2.38 (2H, m), 2.1 (6H, s), 1.33 (6H, t).

b) A solution of N-(2-dimethylaminoethyl)diethylphosphonoformamide (0.903 g), prepared in stage a) above, in acetonitrile (10 ml) was treated with bromotrimethylsilane (2.32 ml) at ambient temperature for 4 h. A few drops of methanol were added to hydrolyze the trimethylsilyl ester and the product was allowed to crystallize from the reaction medium. The product N-(2-dimethylaminoethyl)phosphonoformamide was identified by $^{31}$P and $^1$H nmr spectroscopy. NMR (D$_2$O): $^{31}$P, −2.01 ppm. $^1$H, 3.82 (2H, t, J=6.6 Hz), 3.57, (2H, t, J=6.6 Hz), 3.075 ppm (6H). Examination of its activity on pure MMP2 enzyme gave the IC$_{50}$ value of 25 nM. In the Boyden chamber chemoinvasion assay the compound was active at 1 microMolar concentration.

Example 7

N-(2-[4-morpholino]ethyl)phosphonoformamide betaine a) To a stirred solution of triethyl phosphonothiolformate (1.72 g, 7.6 mmol) in anhydrous acetonitrile (10 ml) was added N-(2-aminoethyl)morpholine (1.1 ml, 8.4 mmol) at room temperature. $^{31}$P NMR monitoring showed that the reaction was complete in 1 h. The volatile by-product EtSH and most of the solvent were removed through distillation.

The residue was purified using the preparative TLC to give a colorless oily product, identified as N-(2-[4-morpholino]ethyl)diethylphosphonoformamide. NMR: (CDCl$_3$): $^{31}$P δ −1.41 ppm. $^1$H: δ 1.18 ppm [t, 6H, ($^3$J$_{HH}$=6.3 Hz), 2.28 (t, 4H, $^3$J$_{HH}$=4.3), 2.33 (t, 2H, $^3$J$_{HH}$=6.2), 3.25 (q, 2H, $^3$J$_{HCCH}$=$^3$J$_{HCNH}$=6.2), 3.49 [t, 4H, $^3$J$_{HH}$=4.3), 4.04 (m, 4H) 7.70 [s (br), 1H].

Anal. Calcd. for C$_{11}$H$_{23}$N$_2$O$_5$P: C, 44.89; H, 7.82; N, 9.51. Found, C, 44.53; H, 7.81; N, 9.40.

b) Bromotrimethylsilane (1.41 ml, 10.9 mmol) was added to a stirred solution of N-(2-morpholinoethyl)diethylphosphonoformamide (0.640 g, 2.2 mmol) prepared in step a) above, in anhydrous acetonitrile (10 ml) at ambient temperature using a syringe. $^{31}$P NMR monitoring showed that formation of the intermediate silyl ester ($^{31}$P NMR: −18.55) was complete in 4 h at ambient temperature. The solvent and the excess bromotrimethylsilane were removed in vacuo, and the residue was dissolved in methanol (5 ml). The solvent was evaporated to dryness under vacuum to give the desired product as a colorless viscous semi-solid (90%). $^{31}$P NMR (D$_2$O): −3.79. Anal. Calcd. for C$_7$H$_{15}$N$_2$O$_5$P. 5.8H$_2$O: C, 24.54; H, 7.76; N, 8.17. Found: C, 25.40; H, 5.43; N, 7.90. In the Boyden chamber chemoinvasion assay the compound was active at 100 μM.

Example 8

N-(2-[1-piperidino]ethyl)phosphonoformamide betaine a) To a stirred solution of triethyl phosphonothiolformate (1.189 g, 5.3 mmol) in anhydrous acetonitrile (10 ml) was added N-(2-aminoethyl)piperidine (0.83 ml, 5.8 mmol) at room temperature and the solution was stirred at room temperature for 3 h. The volatile by-product EtSH and the solvent were removed through distillation. The residue was purified by VLC (vacuum liquid chromatography) using gradient eluents (ethyl acetate/methanol, 95:5 to 50:50) to give N-(2-[1-piperidino]ethyl)diethylphosphonoformamide as a colorless oily product (1.352 g, 87.9%). NMR (CDCl$_3$): $^{31}$P, δ −1.29. $^1$H, 1.20 (t, 6H, $^3$J$_{HH}$=7.2), 1.25 (m, 2H), 1.39 [quintet, 4H, $^3$J$_{HH}$=5.1), 2.22 (t, 4H, $^3$J$_{HH}$=5.1), 2.30 (t, 2H, $^3$J$_{HH}$=5.7), 3.25 (q, 2H, $^3$J$_{HCCH}$=$^3$J$_{HCNH}$=5.7), 4.07 (m, 4H, (br. s 1H).

b) Bromotrimethylsilane (2.63 ml, 20.3 mmol) was added to a stirred solution of N-(2-[1-piperidino]ethyl)diethylphosphonoformamide (1.189 g, 4.1 mmol) prepared in step a) above, in anhydrous acetonitrile (10 ml) at ambient temperature. $^{31}$P NMR monitoring showed that formation of the intermediate silyl ester ($^{31}$P NMR: −18.55) was complete in 4 h at ambient temperature. The solvent and the excess bromotrimethylsilane were-removed in vacuo, and the residue was dissolved in methanol (15 ml). The solvent was evaporated to dryness under vacuum to give the desired product as a colorless viscous semi-solid product (94.4%) NMR (D$_2$O): $^{31}$P −3.37. $^1$H 1.18–1.69 (m, 6H), 2.69 (t, 2H$_{1a}$, $^3$J$_{H1aH2a}$=$^2$J$_{H1aH1e}$=11.5) 3.02 (t, 2H, $^3$J$_{HH}$=6.0), 3.32 (d, 2H, $^2$J$_{H1aH1e}$=11.5), 3.41 (t, 2H, $^3$J$_{HH}$=6.0). In the Boyden chamber chemoinvasion assay the compound was active at 100 μM.

Example 9

N-(2-[1-pyrrolidino]ethyl)phosphonoformamide betaine a) To a stirred solution of triethyl phosphonothiolformate (1.238 g, 5.5 mmol) in anhydrous acetonitrile (10 ml) was added N-(2-aminoethyl)pyrrolidine (0.687 g, 6.1 mmol) at room temperature. $^{31}$P NMR monitoring showed that the reaction was complete in 2 h. The volatile by-product EtSH and the solvent were removed by distillation. The residue was purified by VLC (vacuum liquid chromatography) using gradient eluents (ethyl acetate/methanol, 90:10 to 50:50) to give N-(2-[1-pyrrolidino]ethyl)diethylphosphonoformamide as a colorless oil (0.620 g, 40.7%). NMR, (CDCl$_3$): $^{31}$P δ −3.82 ppm. $^1$H, δ, 1.06 (t, 6H, $^3$J$_{HH}$=6.6), 1.46 (br. s 4H), 2.23 (br. s 4H), 2.34 (t, 2H, J=5.7 Hz) 3.14 (q, 2H, J=5.7), 3.93 [m, 4H) 7.77 [br. s, 1H).

b) Bromotrimethylsilane (1.1 ml, 7.9 mmol) was added to a stirred solution of N-(2-[1-pyrrolidino]ethyl)diethylphosphonoformamide (0.442 g, 1.6 mmol) prepared in step a) above, in anhydrous acetonitrile (10 ml) at ambient temperature using a syringe. The reaction mixture was allowed to stir at ambient temperature, and the progress of the reaction was monitored by $^{31}$P NMR. After 18 h the reaction was completed to give the intermediate silyl ester ($^{31}$P NMR: −18.13). The solvent and the excess bromotrimethylsilane were removed in vacuo, and the residue was dissolved in methanol (15 ml). The solvent was evaporated to dryness under vacuum to give the desired product as a colorless viscous semi-solid (100%). NMR (D$_2$O) $^{31}$P: −5.48 ppm. $^1$H: δ 1.73 (m, 2H), 1.88 (m, 2H), 3.44 (m, 2H), 2.86 (m, 2H), 3.14 (t, 2H, $^3$J$_{HH}$=5.7), 3.40 (t, 2H, $^3$J$_{HH}$=5.7). In the Boyden chamber chemoinvasion assay the compound was active at 100 μM.

Example 10

N-(2-acetamidoethyl)phosphonoformamide a) To a stirred solution of triethyl phosphonothiolformate (1.612 g, 7.1 mmol) in anhydrous acetonitrile (10 ml) was added N-acetylethylenediamine [0.890 g, 7.8 mmol] at room temperature. $^{31}$P NMR monitoring showed that the reaction was complete in 2 h. The volatile by-product EtSH and the solvent were removed by distillation, and the residue was purified by VLC (vacuum liquid chromatography) using gradient eluents [from ethyl acetate/petroleum ether (50:50) to ethyl acetate/methanol (80:20)] to give N-(2-acetamidoethyl)-diethylphosphonoformamide as a colorless oily product (1.217 g, 64.2%). NMR (CDCl$_3$): $^{31}$P −1.77. $^1$H, 1.26 (t, 6H, $^3$J=7.0), 1.87 (s, 3H), 3.34 (m, 4H), 4.13 (m, 4H), 7.09 [br. s, 1H] and 8.31 [br. s), 1H] Anal. Calcd. for C$_9$H$_{19}$N$_2$O$_5$P: C, 40.60; H, 7.14; N, 10.52. Found: C, 40.23; H, 7.35; N, 9.65.

b) Bromotrimethylsilane (3.0 ml, 22.9 mmol) was added to a stirred solution of N-(2-acetamidoethyl)diethylphosphonoformamide (1.217 g, 4.6 mmol) prepared in step a) above, in anhydrous acetonitrile (10 ml) at ambient temperature. The reaction mixture was allowed to stir at ambient temperature for 6 h to yield the intermediate silyl ester ($^{31}$P NMR: −19.30). The solvent and the excess bromotrimethylsilane were removed in vacuo, and the residue was dissolved in methanol (15 ml). The solvent was evaporated to dryness under vacuum to give the desired product as a white solid (100%). NMR (D$_2$O): $^{31}$P −3.25. $^1$H: 1.66 [s, 3H) 3.04 (m, 4H). Anal. Calcd. for C$_5$H$_{11}$N$_2$O$_5$P. 2.1H$_2$O: C, 24.22;

H, 6.13; N, 11.29. Found: C, 24.26; H, 5.18; N, 10.52. In the Boyden chamber chemoinvasion assay the compound was active at 100 μM.

Example 11

N-cyclohexylphosphonothioformamide a) A mixture of 0.359 g (1.4 mmol) of N-(cyclohexyl) diethylphosphonoformamide, 0.276 g (0.7 mmol) of Lawesson Reagent in 10 ml toluene was refluxed for 5.5 h. The resulting mixture was subjected to VLC (vacuum liquid chromatography) using gradient eluants [from 5% ethyl acetate in petroleum ether to ethyl acetate/petroleum ether (40:60) to give N-cyclohexyl diethylphosphonothioformamide as a yellow solid, 0.327 g (85.8%, isolated yield). NMR (CDCl$_3$): $^3$P −1.66. $^1$H, 1.18–2.01 (m, 16H), 4.17 (m, 4H), 4.34 (m, 1H), 8.89 (br. s, 1H).

b) Bromotrimethylsilane (0.69 ml, 5.3 mmol) was added to a stirred solution of N-cyclohexyldiethylphosphonothioformamide (0.298 g, 1.1 mmol) prepared in step a) above, in anhydrous acetonitrile (10 ml) at ambient temperature using a syringe. The reaction mixture was allowed to stir at ambient temperature for 8 h to yield the intermediate silyl ester as a mixture of two geometrical isomers: syn ($^{31}$P NMR: −18.98, 7.2%) and anti isomer ($^{31}$P NMR: −16.86, 92.8%). The solvent and the excess reagent were removed in vacuo, and the residue was dissolved in methanol. Evaporation of the solvent in vacuum gave the desired product as a yellow solid, m. p. 122° C. NMR (CD$_3$OD): $^{31}$P: 0.36 (72%, syn); 2.09 (28%, anti). $^1$H: 1.28–2.01 [m, 10H], 3.83 [s, (br) 0.28H, Hb, anti], 4.39 [s, (br), 0.72H, Ha, syn].

Example 12

Ethyl N-[(2-dimethylethylammonio)ethyl]phosphonoformamide betaine

Diethyl N-(2-dimethylaminoethyl)phosphonoformamide prepared in Example 6, has undergone ethyl group migration from oxygen to nitrogen after standing at ambient temperature for two weeks. Yield: 100%. NMR (D$_2$O): $^{31}$P: −2.53 (t, J=7 Hz). $^1$H, 3.74 (2H, dq, J=7 Hz), 3.50, (2H, t, J=6.3 Hz), 3.23 (4H, m), 2.87 (6H, s) 1.13 (3H, t, J=6.6 Hz), 1.02 (3H, t, J=6.9 Hz).

Example 13

Hydrogen N-[(2-dimethylethylammonioethylcarbamoylphosphonate betaine

To a suspension of the monoethyl ester obtained in Example 12 (0.62 g, 2.45 mmol) in acetonitrile (10 ml) bromotrimethylsilane (1.6 ml, 12.2 mmol) was added, resulting in immediate dissolution of the betaine. After standing at ambient temperature overnight the silylation reaction was complete. The desired product was isolated in quantitative yield after treatment with methanol and evaporation of the solvents and volatile by-products. NMR (D$_2$O): $^{31}$P: −3.81 (s). $^1$H, 3.48 (2H, t, J=6.6 Hz), 3.15–3.24 (4H, m), 2.85 (6H, s), 1.10 (3H, t, J=7.2 Hz).

Example 14

N$^\alpha$-(Phosphonoformyl)phenylalanylmethylamide a) A solution of L-phenylalanylmethylamide trifluoroacetate (0.278 g, 0.95 mmol), triethyl phosphonothiolformate (0.215 g, 0.95 mmol) and diisopropylethylamine (0.165 g, 0.95 mmol) in acetonitrile (5 ml) was stirred at room temperature for 1 month. $^{31}$P nmr showed 94% reaction. The product N$^\alpha$-(Diethylphosphonoformyl)phenylalanylmethylamide was purified by chromatography eluted by 1% MeOH in AcOEt, 150 mg. NMR (CDCl$_3$): $^{31}$P: −4.41. Anal. Calcd. For C$_{15}$H$_{23}$N$_2$O$_5$P: C, 52.63; H, 6.72; N, 8.18. Found: C, 51.78; H, 6.90; N, 7.82.

b) A solution of N$^\alpha$-(diethylphosphonoformyl)phenylalanylmethylamide (0.098 g, 0.286 mmol) prepared in step a) above and bromotrimethylsilane (0.37 ml, 2.86 mmol) was stirred for 3 days. After the reaction mixture was allowed to hydrolyze, the desired product was isolated as a white solid by centrifugation. NMR (D$_2$O+NaHCO$_3$): $^{31}$P: −3.81 (s). $^1$H: 7.13–6.99 (5H, m); 4.32 (1H, t, J=7.2 Hz), 2.84 (2H, m); 2.38 (3H, s). Anal: Calcd. For C$_{11}$H$_{15}$N$_2$O$_5$P. 0.5H$_2$O: C, 44.74, H, 6.1, N, 9.4. Found: C, 44.3, H, 5.4 N, 9.31.

Example 15

Phosphonoformylhistamine YK 104 a) Diisopropylphosphonoformylhistamine

1. To a solution of diisopropyl ethyl phosphonothiolformate (6.11 g) in ethanol (35 ml) was added histamine (2.78 g) and the solution was kept at room temperature for 24 h. Evaporation of the solution gave 6.03 g of a solid, m. p. 90–92° C. NMR (CDCl$_3$), $^{31}$P −3.27 ppm. $^1$H: 7.01 ppm (broad 1H), 7.47 (s, 1H), 6.79 (s, 1H) 4.43 (sext. 2H), 3.61 (t, 2H), 2.82 (t, 2H), 1.32 (dd, 12H). Anal. Calcd. C, 47.52; H, 7.26; N, 13.86. Found: C, 47.55; H, 7.49; N, 14.12.

b) Phosphonoformylhistamine The solution of the diisopropyl ester (6.02 g) in dioxan (30 ml) was treated with bromotrimethylsilane (12.87 ml) at 60° C. overnight. The solution was treated with methanol, evaporated to a foam, m.p 167° C. NMR (D$_2$O) $^{31}$P −3.38 ppm. $^1$H: 8.26 (s, 1H), 7.13 (s, 1H), 3.41 (t, 2H), 2.82 (t, 2H). Anal. Calcd. for C$_6$H$_{10}$N$_3$O$_4$P.2H$_2$O, C, 28.23; H, 5.49; N, 16.47. Found: C, 27.96; H, 4.42; N, 16.02.

Example 16

N-cyclopentylcarbamoylphosphonic acid YK-96 a) Diethyl N-cyclopentylcarbamoylphosphonate

To a solution of triethyl phosphonothiolformate (1.97 g) in acetonitrile 15 ml was added cyclopentylamine (0.82 g) and the solution was kept at room temperature overnight. Evaporation of the solution gave 1.9 g of a oil. Separation by chromatography gave 1.43 g, oil. NMR (CDCl$_3$), $^{31}$P −3.55 ppm. $^1$H: 7.1 ppm (broad 1H), 4.2 (m. 4H), 1.96 (m, 5H), 1.8–1.5 (m, 4H), 1.5–1.4 (m, 2H) 1.33 (t, 6H). Anal. Calcd. for C$_{10}$H$_{20}$NO$_4$P, C, 48.19; H, 8.03; N, 5.62. Found: C, 47.98; H, 7.87; N, 5.92.

b) N-cyclopentylcarbamoylphosphonic acid

The solution of the diethyl ester (1.02 g) in acetonitrile (10 ml) was treated with bromotrimethylsilane (2.24 ml) at r. t. overnight. The solution was treated with methanol and evaporated. The residue was recrystallized from aqueous ethanol to give 0.18 g crystals, m. p. 135–8° C. NMR (D$_2$O) $^{31}$P −2.73 ppm. $^1$H: 3.89 (quin, 1H), 1.75–1.63 (m, 3H), 1.47–1.22 (m, 6H). Anal. Calcd. for C$_6$H$_{12}$NO$_4$P, C, 37.30; H, 6.22; N, 7.25. Found: C, 37.28; H, 6.38; N, 6.92.

Example 17

N-(S-benzylmercaptoethyl)carbamoylphosphonic acid YK-125-I a) Diethyl N-(S-benzylmercaptoethyl)carbamoylphosphonate

To a solution of triethyl phosphonothiolformate (3.2 g) in acetonitrile 30 ml was added S-benzylmercaptoethylamine (2.35 g) and the solution was kept at room temperature 24 h. Evaporation of the solution gave 4.63 g of almost pure reaction product as an oil. Separation by chromatography gave by ethyl acetate-petroleum ether gave 2.848 g oil. NMR (CDCl$_3$) $^{31}$P −0.518 ppm. $^1$H: 7.7 ppm (broad 1 H), 7.2–7.35 (m, 5H) 4.3–4.15 (m, 4H), 3.70 (s, 2H), 3.44 (q, 2H), 2.55 (t, 2H), 1.393 (t, 6H). Anal. Calcd. for C$_{17}$H$_{22}$NO$_4$PS, C, 50.75; H, 6.65; N, 4.23. Found: C, 50.45; H, 6.73; N, 4.08.

b) N-(S-benzylmercaptoethyl)carbamoylphosphonic acid

The solution of the diethyl ester (2.5 g) in acetonitrile (30 ml) was treated with bromotrimethylsilane (10 ml) at r. t. overnight. The solution was treated with methanol and evaporated to give a solid. NMR (D$_2$O), $^1$H: 7.26 (m, 5H), 3.67 (s, 2H), 3.24 (t, 2H), 2.49 (t, 2H). Anal. Calcd. for C$_{13}$H$_{14}$NO$_4$PS, C, 43.63; H, 5.09; N, 5.09. Found: C, 43.24; H, 5.34; N, 4.77.

In the following Example 18, is described a general procedure for the synthesis of phosphonoformylpeptides, such as the compounds in Examples 19, 20 and 21.

Example 18

Phosphonoformyl-Leu-Val-NHMe a) Preparation of Diethylphosphonoformyl-Leu-Val-NHMe

BocLeu-Val-NHMe. (1.00 g, 2.9 mmol) was dissolved in TFA (5 ml), and the solution stirred at room temperature for 1 h. The volatile materials were removed in vacuo, and the residue was dried first by azeotropic removal of H$_2$O with toluene, then in vacuo at room temperature for several hours to give the dry trifluoroacetate salt. HLeuValNHMe. Trifluoroacetate was dissolved in dry DMF (5 ml), treated with triethylamine (0.64 g, 5.8 mmol) and with triethyl phosphonothioformate (1.14 g, 5.0 mmol) and was stirred at room temperature for 3 days. Dichloromethane (50 ml) and distilled water (30 ml) were added, the phases separated and the organic layer washed with 4% aqueous HCl (30 ml), saturated NaHCO$_3$ solution (30 ml), and with saturated NaCl solution (30 ml), dried over anhydrous Na$_2$SO$_4$. Most of the solvent was evaporated in vacuo and the residue was purified by VLC (vacuum liquid chromatography) using gradient eluants (ethyl acetate/acetone, 95:5 to 50:50) to give diethylphosphonoformylLeuValNHMe as a colorless oil (0.86 g, 73%). $^1$H NMR (CDCl$_3$) δ 0.88–0.94 (m, 12H), 1.32–1.39 (m, 6H), 1.50–1.70 (m, 3H), 2.04–2.17 (m, 1H), 2.80 (d, 3H, J=5.1), 4.10–4.29 (m, 5H, one CH overlapping in it), 4.53 (q, 1H, J=6.3), 6.21 (q, 1H, J=4.2), 6.73 (d, 1H, J=8.7), 7.61 (d, 1H, J=8.1). $^{31}$P NMR (CDCl$_3$) δ −2.27.

b) Preparation of Phosphonoformyl-Leu-Val-NHMe

Bromotrimethylsilane (1.25 ml, 9.6 mmol) was added to a stirred solution of diethylphosphonoformylLeuValNHe (0.79 g, 1.9 mmol) in anhydrous acetonitrile (5 ml) at ambient temperature. Stirring the reaction mixture at ambient temperature for 72 h, it yielded the bis(trimethylsilyl) ester, ($^{31}$P NMR: −18.65) which was alcoholyzed by MeOH and evaporated in vacuo. The residue was dried in a desiccator over P$_2$O$_5$ in high vacuo, to give the final product as a pale yellow foam (0.71 g, 100%). NMR $^1$H NMR (D$_2$O) δ 0.64–0.70 (m, 12H), 1.30–1.50 (m, 3H), 1.70–1.84 (m, 1H), 2.48 (s, 3H), 3.75 (d, 1H, J=8.4), 4.23 (dd, 1H, J=7.5, J=4.5). $^{31}$P NMR (D$_2$O) δ −3.60. $^{13}$C NMR D$_2$O+NaHCO$_3$) δ 18.16, 18.35, 21.05, 22.12, 24.21, 25.66, 29.76, 40.26, 51.58 (d, $^3J_{PC}$=5.5), 60.00, 173.61, 174.77, 179.65 (d, $^1J_{PC}$=191.4). MS (ESI) 352.2 (MH$^+$). Analysis C$_{13}$H$_{26}$N$_3$O$_6$P.2H$_2$O: Calcd. C, 40.31; H, 7.75; N, 10.85; P 8.01. Found C 39.93; H, 7.80; N, 10.79; P 7.86. [a]$^{25}_D$−31.7° (c=0.28, MeOH).

Example 19

Phosphonoformyl-Leu-Phe-NHMe was prepared in a similar manner, as Phosphonoformyl-Leu-Val-NHMe and the following physical data was obtained for intermediate and end-product:

a) Diethylphosphonoformyl-Leu-Phe-NHMe

A colorless solid foam $^1$H NMR (CDCl$_3$) δ 0.84 (t, 6H, J=6.3), 0.87 (d, 3H, J=5.7), 1.29–1.35 (m, 6H), 1.40–1.60 (m, 3H), 2.65 (d, 3H, J=4.5), 2.90–3.07 (m, 2H), 4.08–4.26 (m, 4H), 4.52 (q, 1H, J=7.8), 4.62 (q, 1H, J=8.1), 6.34 (q, 1H, J=4.5), 7.13–7.27 (m, 6H, one NH overlapping in it), 7.98 (d, 1H, J=8.1). $^{31}$P NMR (CDCl$_3$) δ −2.17. $^{13}$C NMR (CDCl$_3$) δ 16.19 (d, 2C, $^3J_{PC}$=6.0), 21.71, 22.79, 24.72, 26.06, 38.38, 40.72, 52.14 (d, $^3J_{PC}$=7.5), 54.49, 64.46 (d, $^2J_{PC}$=4.5), 64.55 (d, $^2J_{PC}$=4.5), 126.68, 128.36, 129.21, 136.78, 165.97 (d, $^1J_{PC}$=224.1), 170.99, 71.30.

b) Phosphonoformyl-Leu-Phe-NHMe a pale yellow solid foam (1.61 g, 100%). NMR $^1$H NMR (D$_2$O) δ 0.59 (d, 3H, J=4.8), 0.65 (d, 3H, J=4.8), 1.16–1.31 (m, 2H), 1.40–1.50 (m, 1H), 2.42 (s, 3H), 2.71–2.95 (m, 2H), 4.13 (dd, 1H, J=7.5, J=7.7), 4.30 (dd, 1H, J=7.2, J=7.1), 7.01–7.19 (m, 5H). $^{31}$P NMR (D$_2$O) δ −3.65. NMR (D$_2$O+NaHCO$_3$) δ 20.98, 21.92, 24.04, 25.84, 36.64, 40.09, 52.07 (d, $^3J_{PC}$=5.6), 55.03, 127.01, 128.64, 129.02, 136.54, 173.13, 174.80, 180.24 (d, $^1J_{PC}$=190.8). MS (ESI) 400.2 (MH$^+$). Analysis C$_{17}$H$_{26}$N$_3$O$_6$P.1.5H$_2$O: Calcd. C, 47.89; H, 6.81; N, 9.86; P 7.28. Found C, 47.97; H, 6.84; N, 9.84; P 6.96. [a]$^{25}_D$–20.5 (c=0.27, MeOH).

Example 20

Phosphonoformyl-Leu-Tyr(Me)-NHMe was prepared in a similar manner, as Phosphonoformyl-Leu-Val-NHMe and the following physical data was obtained for intermediate and end-product:

a) Diethylphosphonoformyl-Leu-Tyr(Me)-NHMe

A colorless solid foam $^1$H NMR (CDCl$_3$) δ 0.77 (d, 3H, J=5.1), 0.79 (d, 3H, J=5.7), 1.19–1.27 (m, 6H), 1.40–1.60 (m, 3H), 2.60 (d, 3H, J=3.3), 2.72–2.94 (m, 2H), 3.61 (s, 3H), 4.00–4.20 (m, 4H), 4.52–4.66 (m, 2H), 6.63, 6.66, 6.97, 6.99 (AA'BB' spin system, 4H), 7.01 (br s, 1H), 7.77 (d, 1H, J=8.1), 8.26 (d, 1H, J=7.8). $^{13}$C NMR (CDCl$_3$) δ 16.12 (d, $^3J_{PC}$=6.0), 16.16 (d, $^3J_{PC}$=5.5), 21.70, 22.78, 24.69, 25.99, 37.65, 40.81, 52.01 (d, $^3J_{PC}$=7.0), 54.58, 54.93, 64.35 (d, $^2J_{PC}$=6.6), 64.44 (d, $^2J_{PC}$=7.0), 113.61, 128.76, 130.21, 158.21, 165.83 (d, $^1J_{PC}$=224.1), 171.09, 171.52. $^{31}$P NMR (CDCl$_3$) δ –2.21.

b) Phosphonoformyl-Leu-Tyr(Me)-NHMe

A pale yellow solid foam $^1$H NMR (D$_2$O+NaHCO$_3$) δ 0.56 (d, 3H, J=6.0), 0.62 (d, 3H, J=6.0), 0.95–1.08 (m, 1H), 1.09–1.24 (m, 2H), 2.48 (s, 3H), 2.62–2.97 (m, 2H), 3.58 (s, 3H), 3.97 (dd, 1H, J=7.5, J=6.9), 4.32 (dd, 1H, J=6.6, J=9.3), 6.71, 6.74, 6.97, 6.99 (AA'BB' spin system, 4H). $^{31}$P NMR (D$_2$O+NaHCO$_3$) δ –1.69. $^{13}$C NMR (D$_2$O+NaHCO$_3$) δ 20.74, 21.58, 23.78, 25.63, 35.50, 39.91, 52.05 (d, $^3J_{PC}$=5.7), 54.79, 54.99, 113.75, 128.98, 130.00, 157.31, 173.01, 174.66, 180.14 (d, $^1J_{PC}$=192.5). MS (ESI) 430.1 (MH$^+$). Analysis C$_{18}$H$_{28}$N$_3$O$_7$P.H$_2$O: Calcd. C, 48.32; H, 6.71; N, 9.39; P 6.94. Found C, 48.19; H, 6.65; N, 9.05; P 7.18. [a]$^{25}_D$–29.50° (c=0.20, MeOH).

Example 21

Phosphonoformyl-Phe-Val-CONHMe was prepared in a similar manner, as Phosphonoformyl-Leu-Val-NHMe and the following physical data was obtained for intermediate and end-product:

a) Diethylphosphonoformyl-Phe-Val-CONHMe

A white solid $^1$H NMR (CDCl$_3$) δ 0.83 (d, 3H, J=6.3), 0.86 (d, 3H, J=6.3), 1.15 (t, 3H, J=6.9), 1.22 (t, 3H, J=6.9), 2.03 (m, 1H), 2.69 (c, 3H, J=3.0), 3.05–3.19 (m, 2H), 3.80–3.98 (m, 2H), 4.05–4.10 (m, 2H), 4.33 (dd, 1H, J=8.1, J=8.1), 5.04 (m, 1H), 7.02–7.20 (m, 5H), 7.30 (br s, 1H), 7.89 (d, 1H, J=8.1), 8.35 (br s, 1H). $^{31}$P NMR (CDCl$_3$) δ –1.90. $^{13}$C NMR (CDCl$_3$) δ 16.02 (d, $^3J_{CP}$=6.0), 16.10 (d, $^3J_{CP}$=6.0), 18.35, 19.17, 25.99, 30.98, 37.47, 54.10 (d, $^3J_{CP}$=7.1), 58.76, 63.97 (d, $^2J_{CP}$=6.0), 64.27 (d, $^2J_{CP}$=6.6), 126.62, 128.22, 129.30, 136.56, 165.72 (d, $^1J_{CP}$=223.7), 170.29, 171.71.

b) Phosphonoformyl Phe-Val-CONHMe

A pale yellow solid $^1$H NMR (D$_2$O+NaHCO$_3$) δ 0.62 (d, 3H, J=6.9), 0.64 (d, 3H, J=6.9), 1.71 (m, 1H), 2.42 (s, 3H), 2.76–2.94 (m, 2H), 3.69 (d, 1H, J=7.8), 4.45 (dd, 1H, J=6.9, J=7.1), 7.01–7.15 (m, 5H). $^{31}$P NMR (D$_2$O+NaHCO$_3$) δ –1.73.

$^{13}$C NMR (D$_2$O+NaHCO$_3$) δ 17.73, 18.04, 25.50, 29.73, 37.27, 53.79 (d, $^3J_{PC}$=6.6), 59.46, 126.91, 128.46, 128.97, 135.46, 172.43, 172.64, 179.11 (d, $^1J_{PC}$=191.4).

MS (ESI) 386.1 (MH$^+$). Analysis C$_{16}$H$_{24}$N$_3$O$_6$P.2H$_2$O: Calcd. C, 45.60; H, 6.65; N, 9.97; P 7.36. Found C, 45.63; H, 6.60; N, 9.33; P 7.33. [a]$^{25}_D$–15.4 (c=0.19, MeOH).

Biological Studies

The biological and therapeutic effects of some of the compounds, which may be used in the compositions of the invention, were evaluated in the following models, and will now be exemplified in the following non-limiting examples and summarized in Table 2.

1. "Matrigel Chemoinvasion Assay"

This assay measures the potency of the compounds to repress the invasiveness of cancer cells, by inhibiting the MMPs produced by them. This assay uses a reconstituted basement membrane preparation, which is similar to the natural basement membranes that the tumor cells have to cross, in order to disseminate. The assay has greater predictive value than the one based on the determination of enzyme inhibition using pure enzyme preparation, since it measures the effect of the drug in an environment similar to the in vivo situation. The compounds examined have been added to the invasion or chemotaxis chambers respectively, at various concentrations, and the resulted invasion and migrations were compared to untreated preparations. Table 1 (above) shows the results of preliminary screening of a variety of oxophosphonates and related compounds in this model. Table 2 (below) shows the percentage of inhibition of invasion by the compounds examined at 50 micromolar concentration, in comparison with Batimastat, a well recognized inhibitor of the hydroxamic acid class, synthesized by British Biotech, Ltd. As can be seen in the column headed by "Inhibition of Chemoinvasion" in Table 2, all the compounds listed inhibited chemoinvasion better than Batimastat.

Description of the of the Matrigel Chemoinvasion Experiment a) The chemoinvasion assays were performed in Boyden chambers. Matrigel (25 μg) was dried on a polycarbonated filter (PVP free, Nucleopore). Fibroblast conditioned medium (obtained from confluent NIH-3T3 cells cultured in serum free DMEM) is used as the chemoattractant. Cells were harvested by brief exposure to 1 mM EDTA, washed with DMEM containing 0.1% bovine serum albumin and added to the Boyden chamber (200,000 cells). The chambers were incubated in a humidified incubator at 37° C. in 5% CO$_2$/95% air atmosphere for 6 h in the presence of the indicated concentrations of the various compounds. The cells, which traversed the Matrigel layer and attached to the lower surface of the filter, were stained with Diff Quick (American Scientific Products) and counted.

b) Matrigel outgrowth assay-cells were harvested as described above, and added to a Matrigel layer in a 24 well plate. After attachment, a second layer of Matrigel was added. Upon solidification of the second layer, culture media (1 ml) was added and the plate was incubated as a monolayer culture. The plates were analyzed daily using Hoffman optics. This assay was used to evaluate growth and invasion in the presence of inhibitory factors which may be added into the culture media.

2. Endothelial Cell Tube Formation

Some of our compounds were examined as to their potency to inhibit capillary formation, which is an in vitro model of angiogenesis, an essential step in the development of primary tumor and metastatic lesions. Endothelial cell migration to the newly formed tumor is the initial phase of angiogenesis, and is dependent on MMP expression. Using this assay that measures endothelial cell tube formation, we evaluated the effects of some oxophosphonates on angiogenesis. Table 2 lists results obtained from testing some representative carbamoylphosphonates in this model. The results shown in the column headed by "Inhibition of Capillary formation" indicate that at 50 micromolar concentration these compounds inhibit to the extent of up to 75% tube formation.

Description of the Endothelial Cell Tube Formation Experiment

Endothelial cells are harvested by 1 mM EDTA, and added to a Matrigel layer in a 24 well plate at 50,000 cells per well. After attachment, culture media (1 ml) is added and the plate is incubated as a monolayer culture. The plates are analyzed hourly using Hoffman optics. This assay is used to evaluate inhibitory factors or stimulatory factors on capillary like structure formation, which may be added into the culture media.

3. Tumor Growth and Metastasis in Animal Models

The abilities of some of the novel oxophosphonates to inhibit the formation of metastasis in vivo were examined in the murine melanoma model. In this model, tumor cells were injected into the tail veins of mice, which were then treated by injections of 50 mg/kg daily doses of the compounds examined for 21 days, and then the tumors formed on the lungs of the mice were counted after appropriate fixation. The results from the examination of 4 representative compounds are listed in the column headed by "Inhibition of Metastasis Formation" in Table 2 along with the results obtained for compound SC-44463, a well recognized inhibitor of the hydroxamic acid class, synthesized by G. D. Searle in Chicago. The compounds examined reduce the number of metastasis by 70–75% compared to untreated animals similarly to SC-44463.

TABLE 2

1. Summary of Biological Activity of Selected Compounds

| Name of Compound | % Inhibition of Chemo-invasion 50 uM | % Inhibition of Capillary formation 50 uM | % Inhibition of Metastasis formation 50 mg/kg for 21 d |
|---|---|---|---|
| N-(2-dimethylaminoethyl) phosphonoformamide betaine - Example 6 | 66 | 75 | 73 |
| N-cyclopentylcarbamoyl-phosphonic acid - Example 16 | 65 | 70 | 70 |
| Phosphonoformylhistamine - Example 15 | 15 | ND | ND |
| N-(S-benzylmercaptoethyl)Carbamoylphosphonic acid - Example 17 | 61 | 58 | ND |
| Phosphonoformyl-Leu-Val-NHMe - Example 18 | 38 | 42 | ND |
| Phosphonoformyl-Leu-Phe-NHMe - Example 19 | 55 | 60 | ND |
| Phosphonoformyl-Leu-Tyr(Me)-NHMe - Example 20 | 39 | 38 | 75 |
| Phosphonoformyl-Phe-Val-CONHMe - Example 21 | 41 | ND | ND |

TABLE 2-continued

1. Summary of Biological Activity of Selected Compounds

| Name of Compound | % Inhibition of Chemo-invasion 50 uM | % Inhibition of Capillary formation 50 uM | % Inhibition of Metastasis formation 50 mg/kg for 21 d |
|---|---|---|---|
| Batimastat | 40 | ND | ND |
| SC-44463 | ND | ND | 75 |

ND: not determined

The invention claimed is:

1. A compound of formula I:

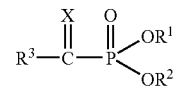

wherein
$R^1$ and $R^2$ are the same and are selected from hydrogen, an alkali metal cation or an optionally substituted ammonium cation;
$R^3$ is —$NHR^4$, where $R^4$ is selected from the group consisting of alkoxyalkyl, hydroxyalkyl, alkoxy, carboxyalkyl, alkoxycarbonylalkyl, aryloxycarbonylalkyl, acyloxy-alkoxycarbonylalkyl, $C_1$–$C_{10}$ aminoalkyl, $C_3$–$C_{10}$ aminocycloalkyl, guanidinoalkyl, guanidinocycloalkyl, amidinoalkyl, or amidinocycloalkyl, or $R^3$ is an amide of an amino acid or an amide of an oligopeptide, and
X is O,
or a pharmaceutically acceptable salt thereof.

2. A compound of formula I:

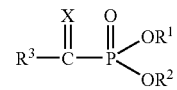

wherein
$R^1$ and $R^2$ are different and are each selected from hydrogen, an alkali metal cation or an optionally substituted ammonium cation;
$R^3$ is —$NHR^4$, where $R^4$ is selected from hydrogen, alkyl substituted with alkoxy or hydroxy, branched alkyl optionally substituted with alkoxy or hydroxy, cycloalkyl optionally substituted, hydroxy, alkoxy, alkoxyalkyl, carboxyalkyl, alkoxycarbonylalkyl, aryloxycarbonylalkyl, acyloxy-alkoxycarbonylalkyl, $C_1$–$C_{10}$ aminoalkyl, $C_3$–$C_{10}$ aminocycloalkyl, guanidinoalkyl, guanidinocycloalkyl, amidinoalkyl or amidinocycloalkyl, or $R^3$ is an amide of an amino acid or an amide of an oligopeptide, and
X is O,
or a pharmaceutically acceptable salt thereof, provided that the compound is not monosodium salt of dimethylaminopropylcarbamoylphosphonic acid.

3. A compound of formula I:

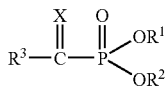

wherein
R$^1$ and R$^2$ are the same and are selected from hydrogen, an alkali metal cation or an optionally substituted ammonium cation;
R$^3$ is —NR$^4$R$^5$, where R$^4$ and R$^5$ may be the same or different and are each selected from hydrogen, alkyl, cycloalkyl, hydroxy, alkoxy, aralkyl, alkoxyalkyl, carboxyalkyl, alkoxycarbonylalkyl, aryloxycarbonylalkyl, acyloxy-alkoxycarbonylalkyl, C$_1$–C$_{10}$ aminoalkyl, C$_3$–C$_{10}$ aminocycloalkyl, guanidinoalkyl, guanidinocycloalkyl, amidinoalkyl or amidinocycloalkyl, or R$^3$ is an amide of an amino acid or an amide of an oligopeptide, and
X is S,
or a pharmaceutically acceptable salt thereof.

4. A compound of formula I:

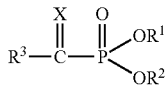

wherein
R$^1$ and R$^2$ are different and are selected from hydrogen, an alkali metal cation or an optionally substituted ammonium cation;
R$^3$ is —NR$^4$R$^5$, where R$^4$ and R$^5$ may be the same or different and are each selected from hydrogen, linear alkyl, cycloalkyl, hydroxy, alkoxy, aralkyl, alkoxyalkyl, carboxyalkyl, alkoxycarbonylalkyl, aryloxycarbonylalkyl, acyloxy-alkoxycarbonylalkyl, heterocyclyl, C$_1$–C$_{10}$ aminoalkyl, C$_3$–C$_{10}$ aminocycloalkyl, guanidinoalkyl, guanidinocycloalkyl, amidinoalkyl or amidinocycloalkyl, or R$^3$ is an amide of an amino acid or an amide of an oligopeptide,
X is S,
or a pharmaceutically acceptable salt thereof.

5. The compound of formula I in claim 2 that is N-(2-acetamidoethyl)phosphonoformamide.

6. The compound of formula I in claim 3 selected from the group consisting of: N-[2-(ethyldimethyl-ammonio)ethyl] thiocarbamoylphosphonate betaine, N-cyclohexylthiocarbamoylphosphonic acid, and N-[2-(dimethylammonio) ethyl]-thiocarbamoylphosphonate betaine.

7. The compound of formula I in claim 1 selected from the group consisting of:
phosphonoformylhistamine, N-(S-benzylmercaptoethyl) carbamoylphosphonic acid, N-[2-(dimethylammonio)ethyl] carbamoylphosphonate betaine, N-[2-(trimethylammonio) ethyl]carbamoylphosphonate betaine, N-phosphonoformylagmatine betaine, N-[3-(trimethylammonio)propyl] carbamoylphosphonate betaine, N-(phosphonoformyl)-phenylalanine N-methylamide, N-phosphonoformyl-Leu-Val-NHMe, N-phosphonoformyl-Phe-Val-NHMe, N-phosphonoformyl-Leu-Phe-N-phenethylamide, N-phosphonoformyl-Leu-Phe-NHMe, N-phosphonoformyl-Leu-Tyr(Me)-NHMe, N-phosphonoformyl-Ala-ProOH, N$^\alpha$-phosphonoformyl-Lys-NHMe, N$^\alpha$-phosphonoformyl-Arg-NHMe, N-phosphonoformyl-Leu-Tyr(Me)-NHMe, N-(cyclohexyl-methyl)carbamoylphosphonic acid, N-cycloheptylcarbamoyl-phosphonic acid, N-(2-aminoethyl)carbamoylphosphonic acid betaine, N-(3-aminopropyl)carbamoylphosphonic acid betaine, N-(4-aminobutyl) carbamoylphosphonic acid betaine, N-(5-aminopentyl)-carbamoylphosphonic acid betaine, and N-(6-aminohexyl) carbamoylphosphonic acid betaine.

8. A pharmaceutical composition comprising as active ingredient a compound of claim 2 together with a pharmaceutically acceptable carrier.

9. A pharmaceutical composition comprising as active ingredient a compound of claim 3 together with a pharmaceutically acceptable carrier.

10. A pharmaceutical composition comprising as active ingredient a compound of claim 4 together with a pharmaceutically acceptable carrier.

11. A pharmaceutical composition comprising as active ingredient a compound of claim 1 together with a pharmaceutically acceptable carrier.

12. The pharmaceutical composition according to claim 11, in an injectable form.

13. The pharmaceutical composition according to claim 11, for oral administration.

* * * * *

UNITED STATES PATENT AND TRADEMARK OFFICE
CERTIFICATE OF CORRECTION

PATENT NO. : 7,101,864 B1
APPLICATION NO. : 10/110317
DATED : September 5, 2006
INVENTOR(S) : Breuer et al.

It is certified that error appears in the above-identified patent and that said Letters Patent is hereby corrected as shown below:

On The Title Page, Item (56), References Cited, insert the following list of references:

FOREIGN PATENT DOCUMENTS

| | | |
|---|---|---|
| DD | 242 811 | 02-11-1987 |
| WO | 99/05148 | 02-04-1999 |
| WO | 89/11285 | 11-30-1989 |
| WO | 95/12604 | 05-11-1995 |
| EP | 0 129 628 | 01-02-1985 |
| EP | 0 003 008 | 07-11-1979 |

On The Title Page Item (56)

OTHER PUBLICATIONS

A.R. GLABE et al., "Novel Functionalized Acylphosphonates as Phosphonoformate Analogs", J. Org. Chem., vol. 61, pp. 7212-7216 (1996)

J.T. DOI et al., "The Synthesis of N-Hydroxyphosphonoformamide, A Potential Antiviral Agent: Inhibition of HIV-1 Reverse Transcriptase", Med Chem Res, vol. 1, pp. 226-229 (1991)

N. LAING et al., "Phosphorus-Containing Inhibitors of Aspartate Transcarbamoylase from *Escherichia Coli*", FEBS Letters, vol. 260, no. 2, pp. 206-208 (January 29, 1990)

T. MORITA et al., "The Preparation of Phosphonic Acids Having Labile Functional Groups", Bulletin of the Chemical Society of Japan, vol. 51(7), pp. 2169-2170 (1978)

T. MORITA et al., "Dealkylation Reaction of Acetals, Phosphonate, and Phosphate Esters with Chlorotrimethylsilane/Metal Halide Reagent in Acetonitrile, and its Application to the Synthesis of Phosphonic Acis and Vinyl Phosphates", Bull. Chem. Soc. Jpn., vol. 54, pp. 267-273 (1981)

L.V. KOVALENKO et al., "Synthesis of (Dialkoxyphosphinoyl)Thioformamides", Russian Journal of General Chemistry, vol. 64, no. 10, part 1, pp. 1460-1461 (1994)

G.H. BIRUM et al., "Total Dealkylation of Esters of Trivalent Phosphorus and Promotion of Anhydride Formation by *N, N, N', N'*-Tetramethylchloroformamidinium Chloride", J. Org. Chem., vol. 37, no. 17, pp. 2730-2733 (1972)

UNITED STATES PATENT AND TRADEMARK OFFICE
CERTIFICATE OF CORRECTION

PATENT NO. : 7,101,864 B1
APPLICATION NO. : 10/110317
DATED : September 5, 2006
INVENTOR(S) : Breuer et al.

It is certified that error appears in the above-identified patent and that said Letters Patent is hereby corrected as shown below:

OTHER PUBLICATIONS (Cont'd)

C.J. SALOMON et al., "Efficient and Selective Dealkylation of Phosphonate Diisopropyl Esters Using $Me_3SIBr$", Tetrahedron Letters, vol. 36, no. 37, pp. 6759-6760 (1995)

M. SEKINE et al., "A General and Convenient Method for the Synthesis of Unesterified Carbamoyl- and Thiocarbamoyl-Phosphonic Acids", Tetrahedron Letters, no. 32, pp. 3013-3016 (1979)

T. MORITA et al., "A Convenient Dealkylation of Dialkyl-Phosphonates by Chlorotrimethylsilane in the Presence of Sodium Iodine", Tetrahedron Letters, no. 28, pp. 2523-2526 (1978)

P.R. BECKETT et al., "Matrix Metalloproteinase Inhibitors", Exp. Opin. Ther. Patents, vol. 8(3), pp. 259-282 (1998) M. MATHEW et al., "Synthesis, Characterization, and Crystal Structure of Dicalcium Glutarylbis(phosphonate) Dihydrate: A Covalently Pillared Layer Structure with the Potential for Epitaxial Growth on Hydroxyapatite". Inorg. Chem., vol. 37, pp. 6485-6494 (1998)

B. LEJCZAK et al., "Plant-Growth-Regulating *N*-(Phosphonoacetyl)amines", Pestic. Sci., vol. 40, pp. 57-62 (1994)

Signed and Sealed this

Twentieth Day of November, 2007

JON W. DUDAS
*Director of the United States Patent and Trademark Office*